United States Patent
Blum et al.

(10) Patent No.: US 7,244,736 B2
(45) Date of Patent: Jul. 17, 2007

(54) TUBULIN INHIBITOR AND PROCESS FOR ITS PREPARATION

(75) Inventors: David Michael Blum, Upper Saddle River, NJ (US); Yanzhong Wu, Bardonia, NY (US); Jean Schmid, Chester, NY (US); Timothy John Doyle, Morristown, NJ (US); Jay Thomas Afragola, Spring Valley, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/451,078

(22) Filed: Jun. 12, 2006

(65) Prior Publication Data
US 2006/0281760 A1    Dec. 14, 2006

Related U.S. Application Data

(60) Provisional application No. 60/690,016, filed on Jun. 13, 2005.

(51) Int. Cl.
*A61K 31/4965*   (2006.01)
*C07D 403/00*    (2006.01)

(52) U.S. Cl. .................................. 514/255.05; 544/295
(58) Field of Classification Search ...................... None
See application file for complete search history.

(56) References Cited

U.S. PATENT DOCUMENTS

| 2003/0092718 A1 | 5/2003 | Haap et al. |
| 2005/0075357 A1 | 4/2005 | Zhang et al. |

FOREIGN PATENT DOCUMENTS

| WO | WO 02/074753 A2 | 9/2002 |
| WO | WO 2005/030216 A1 | 4/2005 |
| WO | WO 2005/030775 A1 | 4/2005 |

OTHER PUBLICATIONS

S. Kushner, et al., J. Amer. Chem. Soc., vol. 74, pp. 3617-3621, 1952.
Eric K. Rowinsky and Anthony W. Tolcher, Cancer Principles & Practice of Oncology, 6th Edition, pp. 431-452, 2001.
Michael M. Gottesman, Annu. Rev. Med., vol. 53, pp. 615-627, 2002.

*Primary Examiner*—Zachary C. Tucker
*Assistant Examiner*—Erich A. Leeser
(74) *Attorney, Agent, or Firm*—Daniel B. Moran

(57) ABSTRACT

The invention provides 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate which is a tubulin inhibitor useful in the treatment of cancer and processes of making hemifumarate compounds and compositioning of the present invention.

47 Claims, No Drawings

TUBULIN INHIBITOR AND PROCESS FOR ITS PREPARATION

CROSS REFERENCE TO RELATED APPLICATION

This application claims benefit of now abandoned U.S. Provisional Patent Applications Ser. No. 60/690,016, filed Jun. 13, 2005, the contents of which are hereby incorporated herein by reference.

FIELD OF THE INVENTION

The present invention relates to a 5-[(trisubstituted)phenyl]-pyrazinylpyrimidine compound which is a tubulin inhibitor useful in the treatment of cancer and a process for its preparation.

BACKGROUND OF THE INVENTION

There is still a need in the art for cytotoxic agents for use in cancer therapy. Antimicrotubule drugs are a major category of anticancer agents (Rowinsky, E. K., and Tolcher, A. W. Antimicrotubule agents. In: V. T. Devita, Jr., S. Hellman, and S. A. Rosenberg (eds.), Cancer Principles and Practice, Ed. 6, pp. 431–452. Philadelphia: Lippincott Williams and Wilkins, 2001). Antimicrotubule drugs work by interfering with the function of cellular microtubules, particularly the mitotic spindle. The disruption of normal spindle function leads to apoptotic cell death.

Many tumors are inherently resistant (e.g., colon tumors) or become resistant after multiple cycles of treatment, at least in part due to the expression of drug transporters located in cancer cell membranes that pump the drugs out of cells and thereby decrease their efficacy (Gottesman, M. M. Mechanisms of cancer drug resistance. Annu. Rev. Med., 53: 615–627, 2002). The best known of these transporters is P-glycoprotein. Accordingly, there is a need for new agents with taxane-like effects on microtubule polymerization that are not substrates of P-glycoprotein or other such pumps and that therefore will overcome this cause of taxane resistance in patients.

Accordingly, there is ongoing research for new clinical candidates. There is also a search for new and improved methods of preparation of those selected clinical candidates.

The preparation and use of 5-phenylpyrimidines having the following general formula

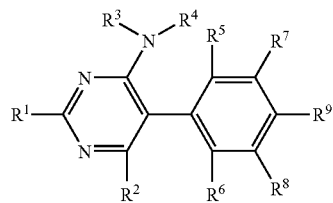

as fungicides are disclosed in WO02/074753 A2.

The preparation and use of 4-amino-2-(pyrin-2-yl)pyrimidines having the following general formula

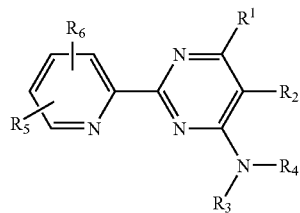

as microbicidal active substances are disclosed in US 2003/0092718 A1.

Published patent application US2005-0075357A1 describes 5-arylpyrimidines as anticancer agents. The reference discloses 6-chloro-5-{2,6-difluoro-4-[3-(methylamino)proxy]phenyl}-2-pyrazin-2-yl-N-[(1S)-2,2,2-trifluoro-1-methylethyl]pyrimidin-4-amine and its hydrochloride. The hydrochloride has been found to have the disadvantage of being very hygroscopic.

The present invention overcomes the disadvantage of the hygroscopicity of the hydrochloride salt.

SUMMARY OF THE INVENTION

The present invention is based upon the unexpected discovery that the selection of the hemifumarate salt of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine essentially avoids the disadvantage of the hygroscopic character associated with the hydrochloride.

The present invention in one embodiment concerns 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate.

In another embodiment of the invention there is provided a process for the preparation of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate; which process comprises:

reacting 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine of the formula

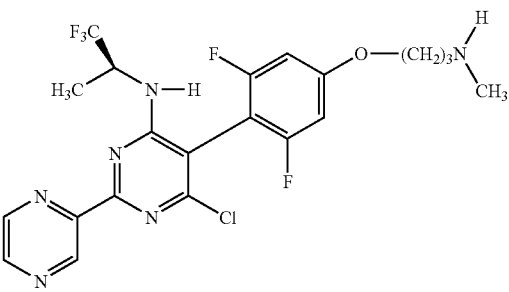

in an aprotic solvent with fumaric acid in an alcohol to give said hemifumarate.

In a further embodiment the invention also concerns a process for the preparation of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate; which process comprises the steps of:

a. reacting pyrazine-2-carbonitrile with base A in an alcohol and treating with an ammonium salt of an inorganic acid to give pyrazine-2-carboxamidine inorganic acid salt;

b. reacting the pyrazine-2-carboxamidine inorganic acid salt with a malonic acid ester of the formula

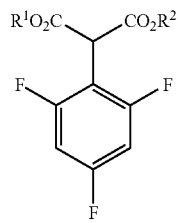

where $R^1$ and $R^2$ are independently $C_1$–$C_3$ alkyl in an aprotic solvent in the presence of a base and acidifying to obtain 2-pyrazin-2-yl-5-(2,4,6-trifluoro-phenyl)-pyrimidine-4,6-diol of the formula

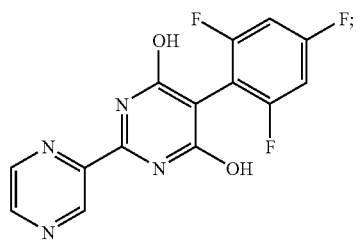

c. chlorinating the 2-pyrazin-2-yl-5-(2,4,6-trifluoro-phenyl)-pyrimidine-4,6-diol with phosphorus oxychloride ($POCl_3$) as chlorinating reagent in the presence of an amine base in an aprotic solvent to give 4,6-dichloro-2-pyrazin-2-yl-5-(2,4,6-trifluoro-phenyl)-pyrimidine of the formula

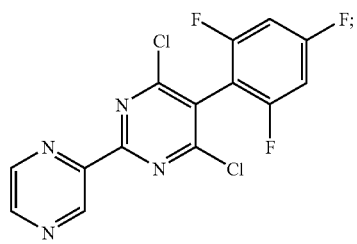

d. reacting the 4,6-dichloro-2-pyrazin-2-yl-5-(2,4,6-trifluoro-phenyl)-pyrimidine with (S)-2,2,2-trifluoro-1-methyl-ethylamine having the formula

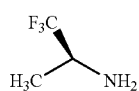

in an aprotic solvent to give 6-chloro-2-pyrazin-2-yl-N-[(1S)-2,2,2-trifluoro-1-methylethyl]-5-(2,4,6-trifluorophenyl)pyrimidin-4-amine having the formula

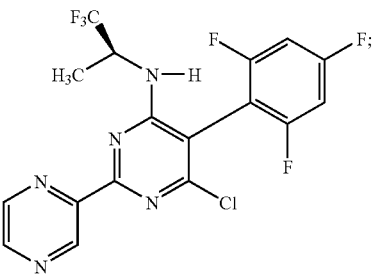

e. reacting 3-methylamino-propan-1-ol with base B in an aprotic solvent and adding 6-chloro-2-pyrazin-2-yl-N-[(1S)-2,2,2-trifluoro-1-methylethyl]-5-(2,4,6-trifluorophenyl)pyrimidin-4-amine to give 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine of the formula

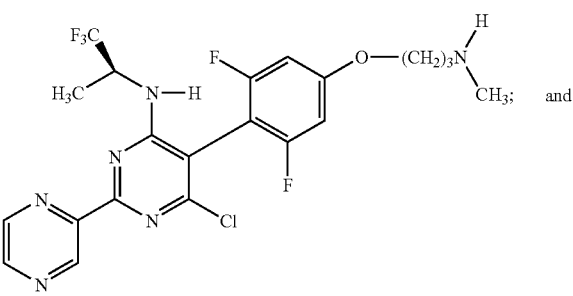

and f. reacting the 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine in an aprotic solvent with fumaric acid in an alcohol to give said hemifumarate.

6-Chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine may also be called S-{6-chloro-5-[2,6-difluoro-4-(3-methylamino-propoxy)-phenyl]-2-pyrazin-2-yl-pyrimidin-4-yl-(2,2,2-trifluoro-1-methyl-ethyl)-amine.

In particular, an embodiment of the invention is a process for the preparation of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate which comprises the steps of:

a. reacting pyrazine-2-carbonitrile with sodium methoxide in methyl alcohol and treating with ammonium chloride to give pyrazine-2-carboxamidine hydrochloride;

b. reacting pyrazine-2-carboxamidine hydrochloride with a malonic acid diethyl ester of formula

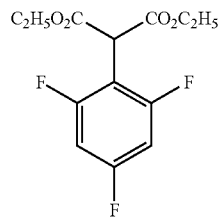

in diglyme in the presence of potassium carbonate and acidifying to give 2-pyrazin-2-yl-5-(2,4,6-trifluorophenyl)-pyrimidine-4,6-diol of the formula

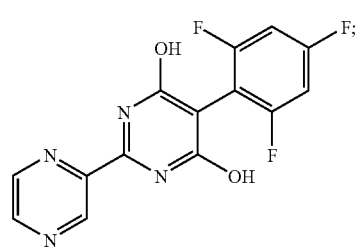

c. halogenating the 2-pyrazin-2-yl-5-(2,4,6-trifluoro-phenyl)-pyrimidine-4,6-diol with phosphorous oxychloride in the presence of N,N-diisopropylethylamine in toluene to give 6-dichloro-2-pyrazin-2-yl-5-(2,4,6-trifluoro-phenyl)-pyrimidine of the formula

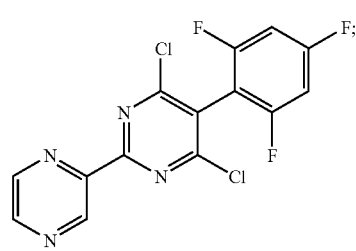

d. reacting the 6-dichloro-2-pyrazin-2-yl-5-(2,4,6-trifluoro-phenyl)-pyrimidine with (S)-2,2,2-trifluoro-1-methyl-ethylamine having the formula

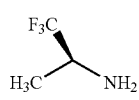

in 1-methyl-2-pyrrolidinone to give 6-chloro-2-pyrazin-2-yl-N-[(1S)-2,2,2-trifluoro-1-methylethyl]-5-(2,4,6-trifluorophenyl)pyrimidin-4-amine of the formula

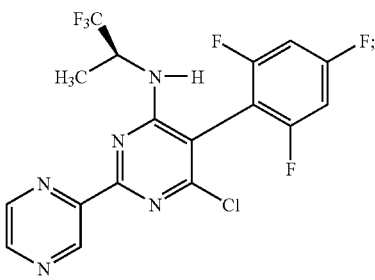

e. reacting an aminoalcohol HO—(CH$_2$)$_3$—NHCH$_3$ with potassium t-butoxide in tetrahydrofuran and adding the 6-chloro-2-pyrazin-2-yl-N-[(1S)-2,2,2-trifluoro-1-methylethyl]-5-(2,4,6-trifluorophenyl)pyrimidin-4-amine to give 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine of the formula

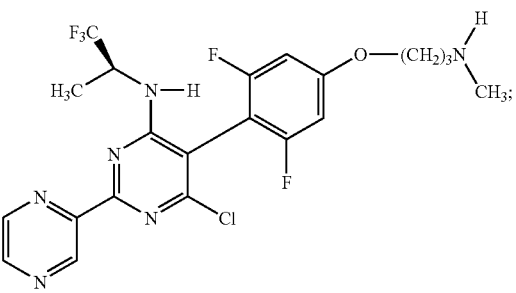

f. reacting 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine in ethyl acetate with fumaric acid in ethyl alcohol to give said hemifumarate.

A particular embodiment of the invention is a process for the preparation of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate which process comprises the steps of:

a. reacting an aminoalcohol HO—(CH$_2$)$_3$—NHCH$_3$ with potassium t-butoxide in tetrahydrofuran and adding the 6-chloro-2-pyrazin-2-yl-N-[(1S)-2,2,2-trifluoro-1-methylethyl]-5-(2,4,6-trifluorophenyl)pyrimidin-4-amine of the formula

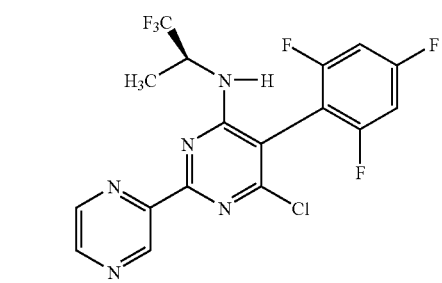

to give 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine of the formula

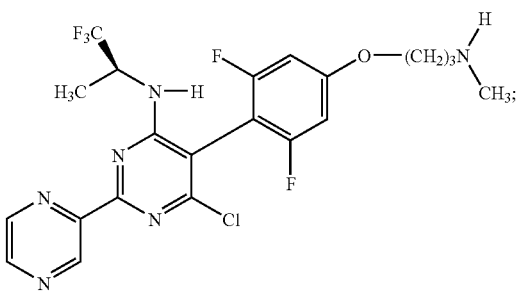

b. adding a solution of fumaric acid in ethyl alcohol to a solution of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine in ethyl acetate to give said hemifumarate and c. isolating said hemifumarate.

Preferably the ratio of ethyl acetate to ethyl alcohol is 1:1 V/V.

The absolute configuration of any compound including the compound of this invention may be determined by conventional X-ray crystallography.

The present invention provides 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate which is useful in cancer treatment and methods for synthesizing said hemifumarate.

The present invention provides a method of treating or inhibiting the growth of cancerous tumor cells and associated diseases in a mammal by administering an effective amount of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate.

The present invention further provides a pharmaceutical composition which comprises an effective amount of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate together with a pharmaceutically acceptable carrier.

The invention further provides the compound 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate produced by the process which comprises:

a. reacting an aminoalcohol HO—(CH$_2$)$_3$—NHCH$_3$ with potassium t-butoxide in tetrahydrofuran and adding 6-chloro-2-pyrazin-2-yl-N-[(1S)-2,2,2-trifluoro-1-methylethyl]-5-(2,4,6-trifluorophenyl)pyrimidin-4-amine of the formula

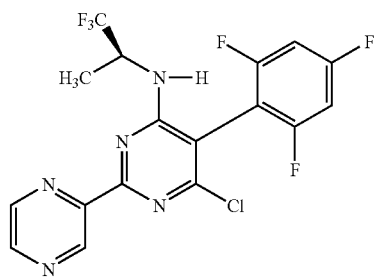

at ambient temperature to give 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine of the formula

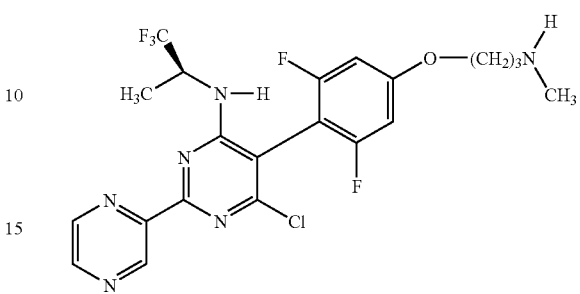

b. adding a solution of fumaric acid in ethyl alcohol to a solution of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine in ethyl acetate to give said hemifumarate; and c. isolating said hemifumarate.

DEFINITIONS

The term alkyl means a straight or branched alkyl of 1 to 3 carbon atoms.

Halogenating agent, means the chlorinating agent, phosphorus oxychloride (POCl$_3$).

Aprotic solvents include N,N-dimethylformamide, 1-methyl-2-pyrrolidinone and diglyme. In some embodiments of the invention aprotic solvents further include tetrahydrofuran (THF) or toluene. In further embodiments of the invention aprotic solvents include toluene and ethyl acetate.

Alkali metal hydride includes lithium, potassium or sodium hydride.

Alkali metal alkoxide includes lithium, potassium or sodium alkoxide. In some embodiments of the invention alkali metal alkoxide includes potassium t-butoxide.

Alcohol includes methyl, ethyl and isopropyl alcohols.

A base is selected from an alkali metal hydroxide, alkali metal carbonate, and an alkali metal hydride. In some embodiments of the invention the alkali metal carbonate is sodium or potassium carbonate. A preferred embodiment is potassium carbonate.

Base A is an alkali metal alkoxide or alkali metal hydroxide.

Base B is an alkali metal alkoxide or an alkali metal hydride. In some embodiments of the invention an alkali metal alkoxide is preferably potassium t-butoxide and an alkali metal hydride is preferably sodium hydride.

An amine base is selected from 1,8-diazabicyclo[4.3.0]non-5-ene(DBU), N,N-diisopropylethylamine, tributylamine and triethylamine.

Ammonium salts of an inorganic acid include ammonium chloride, ammonium bromide, ammonium sulfate, ammonium phosphate and ammonium nitrate.

Inorganic acid salts include hydrochlorides, hydrobromides, sulfates, hydroiodides and nitrates.

DETAILED DESCRIPTION OF THE INVENTION

Reaction scheme 1 of the present invention illustrates the process of preparing 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate (I).

and more preferably sodium methoxide in a ratio of about 1:1 (mole/mole) in the temperature range of about 20–40° C., preferably in the range of about 28–32° C. for about 3–12 h, preferably in the range of 4–5 h, followed by treating with an ammonium salt of an inorganic acid, for example, ammonium chloride for a period of about 16–48 h, preferably in the range of 20–24 h at about 25° C. or optionally for about

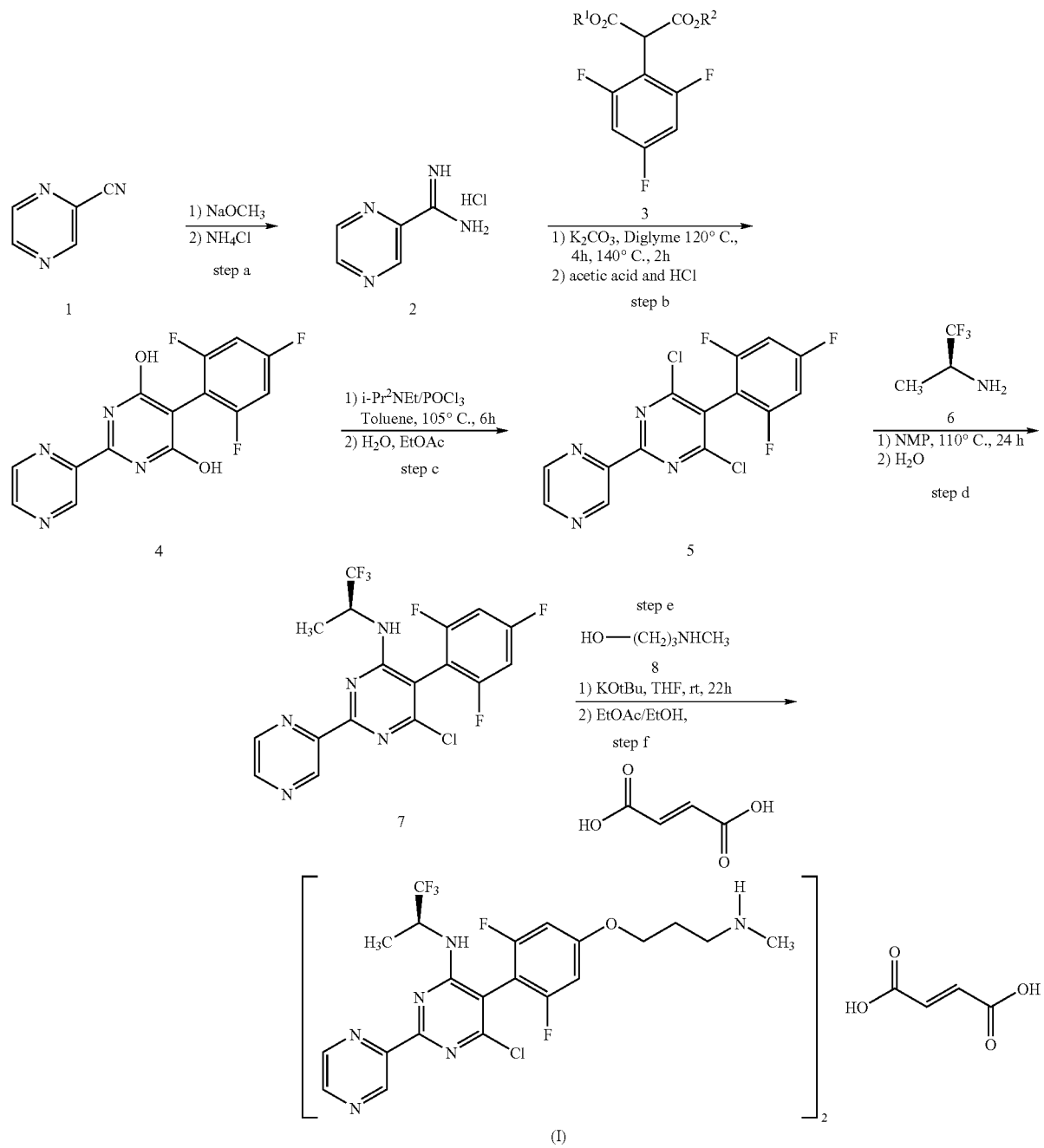

According to Scheme 1, step a, pyrazine-2-carbonitrile 1 is reacted in an alcohol solvent, preferably methyl alcohol in the presence of base A selected from an alkali metal hydroxide or alkali metal alkoxide, preferably sodium methoxide 3–6 h at reflux. Methyl t-butyl ether is added and the mixture is stirred for about 15 to 30 min and the solid which forms is collected by filtration, washed with methyl t-butyl ether then dried at about 40° C. under vacuum to give pyrazine- 2-carboxamidine hydrochloride 2 as a white solid. Optionally following reflux the volatiles are removed to a residue and the residue is crystallized from ethanol-diethyl ether and the product collected. In particular, the procedure described has higher yields as compared to the art (S. Kushner et al, J. Amer. Chem. Soc., 74, 3617–3621 (1952) and published patent application US2005-0075357A1).

In scheme 1, step b, 2-(2,4,6-trifluoro-phenyl)-malonic acid diester 3 wherein $R^1$ and $R^2$ are independently alkyl of 1 to 3 carbon atoms, preferably ethyl is reacted with pyrazine-2-carboxamidine hydrochloride 2 in a ratio of about 1:1 to 1:1.5 mole/mole, preferably in the range of 1:1.2 mole/mole in the presence of a base selected from an alkali metal hydroxide, alkali metal carbonate, and an alkali metal hydride or optionally an amine base selected from 1,8-diazabicyclo[4.3.0]non-5-ene(DBU), N,N-diisopropylethylamine and triethylamine in an aprotic solvent to form the 2-pyrazin-2-yl-5-(2,4,6-trifluoro-phenyl)-pyrimidine-4,6-diol 4. In a preferred embodiment the base is an alkali metal carbonate. In a more preferred embodiment the base is potassium carbonate in a ratio of 1:1.2 mole/mole in diglyme or alternatively a ratio of 1:2 mole/mole for DBU in 1-methyl-2-pyrrolidinone (NMP). In a preferred embodiment the aprotic solvent is selected from N,N-dimethylformamide, 1-methyl-2-pyrrolidinone (NMP) and 2-methoxyethyl ether (diglyme), more preferably, diglyme and NMP, at a temperature range of about 80° to 180° C., preferably 120–140° C. in diglyme with potassium carbonate and preferably about 95° C. in NMP with DBU for about 3–10 h, preferably in the range of 4–6 h to form the 2-pyrazin-2-yl-5-(2,4,6-trifluoro-phenyl)-pyrimidine-4,6-diol 4. The reaction mixture in diglyme with potassium carbonate is cooled to 25–30° C., water is added, followed by the addition of acetic acid followed by aqueous HCl or other mineral acid to a pH of about 1–3, preferably about 2–3 forming a solid which is filtered, washed with water and optionally washed with isopropyl alcohol respectively. The solid is dried at about 60° C./0–10 mmHg for about 24 h to give 2-pyrazin-2-yl-5-(2,4,6-trifluoro-phenyl)-pyrimidine-4,6-diol 4 as a solid which is used directly for the next step.

The reaction mixture under the alternative conditions of amine base DBU with aprotic solvent NMP is cooled to about 50° C. and aqueous HCl is added forming a solid, which is filtered and washed with water. The solid is dried at about 60° C./0–10 mmHg for about 24 h to give 2-pyrazin-2-yl-5-(2,4,6-trifluoro-phenyl)-pyrimidine-4,6-diol 4 as a solid which is used directly for the next step.

According to scheme 1, step c, to a mixture of 2-pyrazin-2-yl-5-(2,4,6-trifluoro-phenyl)-pyrimidine-4,6-diol 4 in an aprotic solvent preferably toluene (g/ml) preferably 5–15 parts, more preferably in 5–10 parts, most preferable in 7 parts, is slowly added at about 10–15° C., phosphorus oxychloride. Following complete addition of the phosphorus oxychloride, N,N-diisopropylethyl amine in a molar ratio of about 1:1 to 1:5, preferably in the range of 1:4 is slowly added at about 10–15° C. and the mixture heated to reflux for about 6 to 24 h, preferably about 6 h. The volatiles are removed by distillation to a residue which is further distilled with toluene preferably two times to afford a further residue. The further residue is dissolved in a solvent selected from ethyl acetate, dichloromethane and toluene, preferably ethyl acetate then partitioned by pouring into water while maintaining the temperature between about 5–15° C. The solvent layer is separated, washed with water, dried over sodium sulfate and filtered through a pad of filter aid such as diatomaceous earth or through hydrous magnesium silicate and most of the volatiles removed to a residue to which is added heptane forming a precipitated product. The precipitated product 4,6-dichloro-2-pyrazin-2-yl-5-(2,4,6-trifluorophenyl)-pyrimidine 5 is collected and having a purity of >95% as shown by high pressure liquid chromatography (HPLC). Further, the 4,6-dichloro-2-pyrazin-2-yl-5-(2,4,6-trifluoro-phenyl)-pyrimidine 5 is formed and isolated without chromatography.

In scheme 1, step d, a solution of 4,6-dichloro-2-pyrazin-2-yl-5-(2,4,6-trifluoro-phenyl)-pyrimidine 5 in an aprotic solvent, preferably 1-methyl-2-pyrrolidinone (NMP) in a ratio of 1–10 mL NMP/g of 4,6-dichloro-2-pyrazin-2-yl-5-(2,4,6-trifluoro-phenyl)-pyrimidine 5, preferably 1–5 mL NMP/g of 4,6-dichloro-2-pyrazin-2-yl-5-(2,4,6-trifluorophenyl)-pyrimidine 5, most preferably 1 mL NMP/g of 4,6-dichloro-2-pyrazin-2-yl-5-(2,4,6-trifluoro-phenyl)-pyrimidine 5 is added (S)-2,2,2-trifluoro-1-methyl-ethylamine 6 in a mole ratio of 4,6-dichloro-2-pyrazin-2-yl-5-(2,4,6-trifluoro-phenyl)-pyrimidine 5 to (S)-2,2,2-trifluoro-1-methyl-ethylamine 6 is 1:2–1:3 (mole/mole) preferably 1:2.5 (mole/mole) with stirring for over 24–48 h, preferably about 24 hours in a temperature range of about 90–125° C., more preferably at about 110° C. for about 24 hours. In an optional embodiment of the invention, the reaction is sealed to prevent loss of (S)-2,2,2-trifluoro-1-methyl-ethylamine 6. The reaction mixture is diluted with isopropyl alcohol (IPA), IPA to NMP (V/V) of about 1:1–1:5 preferable at about 1:3, then water is added with stirring at about 10–20° C. in a ratio of NMP to water (v/v) of about 1:1–1:5 (v/v), preferably at about 1:3 (v/v) with about 30 minutes of additional stirring and collecting, without the need of chromatography, the solid product, washing with water and drying to give 6-chloro-2-pyrazin-2-yl-N-[(1S)-2,2,2-trifluoro-1-methyl-ethyl]-5-(2,4,6-trifluorophenyl)pyrimidin-4-amine 7. In a preferred embodiment of the invention, 4,6-dichloro-2-pyrazin-2-yl-5-(2,4,6-trifluorophenyl)-pyrimidine in 1-methyl-2-pyrrolidinone (NMP) is treated with (S)-2,2,2-trifluoro-1-methyl-ethylamine at about 110° C. for about 24 h and the reaction mixture diluted with IPA, then water 1:3 (v/v) is added slowly forming a precipitated product. The precipitated product is filtered, washed with water, and dried to give a solid product in 92% yield, having a 96% HPLC purity and an enantiomeric excess of >99%. The product 6-chloro-2-pyrazin-2-yl-N-[(1S)-2,2,2-trifluoro-1-methyl-ethyl]-5-(2,4,6-trifluorophenyl)pyrimidin-4-amine 7 is collected without the need for chromatography.

In scheme 1, step e, to a solution of a base B selected from alkali metal alkoxide preferably potassium t-butoxide or a suspension of alkali metal hydride preferably sodium hydride (60% in mineral oil) in an aprotic solvent preferably anhydrous tetrahydrofuran (THF), optionally dimethylsulfoxide (DMSO) is added amino alcohol HO—$(CH_2)_3$—$NHCH_3$ dropwise at a temperature range of about 10–40° C. preferably at about 23° C. for about 30 minutes wherein the ratio of aprotic solvent to aminoalcohol is preferably about 5 mL THF/g of aminoalcohol HO—$(CH_2)_3$—$NHCH_3$. A solution of 6-chloro-2-pyrazin-2-yl-N-[(1S)-2,2,2-trifluoro-1-methylethyl]-5-(2,4,6-trifluorophenyl)pyrimidin-4-amine 7 in tetrahydrofuran, preferably, in a ratio of THF to 6-chloro-2-pyrazin-2-yl-N-[(1S)-2,2,2-trifluoro-1-methyl-ethyl]-5-(2,4,6-trifluorophenyl)pyrimidin-4-amine 7 of about 2 mL of THF/g is added over about 10–30 min. The mixture is stirred at 23±2° C. for about 18–40 h, preferably about 24 h. The reaction mixture is added to cold water at about 5–15° C., preferably about 10° C., in a ratio of water to 6-chloro-2-pyrazin-2-yl-N-[(1S)-2,2,2-trifluoro-1-methylethyl]-5-(2,4,6-trifluorophenyl)pyrimidin-4-amine 7 of about 14 mL/g. The reaction mixture is extracted with ethyl acetate or toluene and the organic phase of ethyl acetate or toluene, preferably ethyl acetate is separated, washed with water and dried. In step f, a solution of fumaric acid in ethanol is added to the organic phase preferably ethyl acetate in a more preferred ratio of 1:1 (V/V) to give the pharmaceutically acceptable hemifumarate salt which is collected. The overall yield is 80–90% with a purity of ~98% HPLC. Optionally steps e and f may be combined in a single step.

Also provided by this invention is a pharmaceutical composition which comprises 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate in association or combination with a pharmaceutically acceptable carrier. Additionally this invention provides a method of treating, inhibiting the growth of, or eradicating a tumor in a mammal in need thereof, wherein said tumor is resistant to at least one chemotherapeutic agent, which comprises administering to said mammal an effective amount of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate.

The effective dosage of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate employed may vary depending on the mode of administration and severity of the condition being treated. However, in general satisfactory results are obtained when administered in amounts ranging from about 0.10 to about 100 mg/kg of body weight per day. A preferred regimen for optimum results would be from about 1 mg to about 20 mg/kg of body weight per day and such dosage units are employed that a total of from about 70 mg to about 1400 mg of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate for a human subject of about 70 kg of body weight are administered in a 24 hour period.

The dosage regimen may be adjusted to provide the optimum therapeutic response. For example, several divided doses may be administered daily or the dose may be proportionally reduced as indicated by the exigencies of the therapeutic situation. A decidedly practical advantage is that 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate may be administered in any convenient manner such as by the oral, intravenous, intramuscular or subcutaneous routes.

The 6-chloro-5-(2,6-difluoro-4-[3-(methylamino)propoxy]phenyl}-2-pyrazin-2-yl-N-[(1S)-2,2,2-trifluoro-1-methylethyl]pyrimidin-4-amine hemifumarate may be orally administered, for example, with an inert diluent or with an assimilable edible carrier, or they may be enclosed in hard or soft shell gelatin capsules, or may be compressed into tablets or they may be incorporated directly with the food of the diet. For oral therapeutic administration, 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate may be incorporated with excipients and used in the form of ingestible tablets, buccal tablets, troches, capsules, elixirs, suspensions, syrups, wafers and the like. Such compositions and preparations should contain at least 0.1% of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate. The percentage of the compositions and preparations may, of course, be varied and may conveniently be between about 2% to about 60% of the weight of the unit. The amount of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate in such therapeutically useful compositions is such that a suitable dosage will be obtained. Preferred compositions or preparations according to the present invention are prepared so that an oral dosage unit form contains between 10 and 1000 mg of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose, or saccharin may be added or a flavoring agnet such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate, sucrose, as a sweetening agent, methyl and propylparabens as preservatives, a dye and flavoring such as cherry or orange flavor. Of course, any material used in preparing any dosage unit form should be pharmaceutically pure and substantially non-toxic in the amounts used.

6-Chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate may also be administered parenterally or intraperitoneally. Solutions or suspensions can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth or microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be prepared against the contaminating action of microorganisms such as bacteria and fungi. The carrier can be a solvent or dispersion medium containing, for example, water, ethanol, polyol (e.g., glycerol, propylene glycol and liquid poly-ethylene glycol), suitable mixtures thereof, and vegetable oils.

Intravenous administration is a preferred manner of administration of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate. For intravenous administration examples of non-limiting suitable carriers include physiological saline, bacteriostatic water, Cremophor EL™ (BASF, Parsippany, N.J.) or phosphate buffered saline (PBS). The composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

The following examples are presented to illustrate certain embodiments of the present invention, but should not be construed as limiting the scope of this invention.

EXAMPLE 1

Pyrazine-2-carboxamidine hydrochloride

To a solution of sodium methoxide ($NaOCH_3$) (51.4 g, 0.952 mol) in methanol (3800 ml) there is added cyanopyrazine (1.00 KG, 9.53 mol) slowly at room temperature. The mixture is heated to 30° C. and stirred for 6 h. The mixture is cooled to 25° C. followed by the addition of ammonium chloride ($NH_4Cl$) (572 g, 10.5 mol). The reaction mixture is stirred for 22 h and methyl t-butyl ether (4000 mL) is added and the mixture is stirred for 15 min forming a solid. The solid is filtered and washed with methyl t-butyl ether (2×1000 mL) then dried at 40° C./0–10 mmHg for 17 h to give white solid product (1435 g) in 95% yield with 95% HPLC purity. $^1$H NMR (DMSO-$D_6$): δ 9.7 (bs, 3H), 9.49 (d, 1H, J=1.5 Hz), 9.04 (m, 1H), 8.93 (t, 1H, J=1.5 Hz)

EXAMPLE 2

2-pyrazin-2-yl-5-(2,4,6-trifluoro-phenyl)-pyrimidine-4,6-diol

A mixture of 2-(2,4,6-trifluoro-phenyl)-malonic acid diethyl ester (200 g, 0.67 mol), pyrazine-2-carboxamidine hydrochloride (132 g, 0.828 mol) and potassium carbonate (114 g, 0.828 mol) in 2-methyoxyethyl ether (diglyme, 600 mL) is heated to 120° C. and stirred for 4 h, then heated to 140° C. and stirred for an additional 2 h. The mixture is cooled to room temperature (25–30° C.) and water (1200 mL) is added over about 15 min. Acetic acid (50 g) is added over 15 min. and 82 ml of concentrated HCl is added over 15 min and the mixture is stirred for about 15 min. at room temperature at a pH of about 2–3. The solid is filtered and washed with water (2×400 mL) and isopropyl alcohol (IPA) (400 mL) and dried at 60° C./10 mmHg for 24 h to give a white solid 69% yield with 95% HPLC purity. $^1$H NMR (DMSO-$d_6$): d 12.45 (bs, 2H), 9.41(s,1H), 8.91(s,1H), 8.46 (m, 1H), 7.23(m, 2H).

EXAMPLE 3

2-pyrazin-2-yl-5-(2,4,6-trifluoro-phenyl)-pyrimidine-4,6-diol 1,8-diazabicyclo[5.4.0]undec-7-ene (DBU; 14.4 g, 0.0944 mol) is added to a mixture of 2-(2,4,6-triflorophenyl) malonic acid diethyl ester (14.3 g, 0.0472 mol) and pyrazine-2-carboxamidine hydrochloride (9.00 g, 0.0566 mol) in 1-methyl-2-pyrrolidinone (NMP; 50 mL) solvent. The resulting mixture is heated to 95° C. while stirring for 7 hours. The mixture is cooled to about 50° C. and then HCl solution (37%, 5.6 mL) is added dropwise, keeping the temperature below 50° C. The mixture is then allowed to cool to about 20° C. Water (50 mL) is added dropwise over 20 minutes, causing the product to precipitate as a solid from the mixture (20–25° C.). The solid is collected by filtration, and the product cake is washed with water (300 mL). The solid is allowed to dry at 23° C. under atmospheric pressure for 24 hours, giving a yellow solid (11.5 g, 97% HPLC area, 76% yield. $^1$H NMR (DMSO-$d_6$): d 12.45 (bs, 2H), 9.41 (s,1H), 8.91(s,1H), 8.46(m, 1H), 7.23(m, 2H).

EXAMPLE 4

4,6-dichloro-2-pyrazin-2-yl-5-(2,4,6-trifluoro-phenyl)-pyrimidine

To a mixture of 2-pyrazin-2-yl-5-(2,4,6-trifluoro-phenyl)-pyrimidine-4,6-diol (228 g, 0.713 mol) in toluene (1600 mL) there is added phosphorus oxychloride (682 mL) at 10–15° C. over 30 min. The mixture is cooled 10° C. and diisopropylethyl amine (367 g, 2.85 mol) is added dropwise over 30 min and then the mixture is heated to reflux for about 6 h. The solvent is removed by distillation to a residue and the residue distilled with toluene (2×500 mL). Then, the residue is dissolved into ethyl acetate (EtOAc) (1000 mL) and the resulted mixture is poured into water (3000 g) while maintaining the temperature between 5–15° C. The reaction mixture is filtered through a pad of diatomaceous earth. The organic phase is separated and the aqueous phase is extracted with EtOAc (1000 mL). The combined organic phase is washed with water (1000 mL), dried over $Na_2SO_4$ and filtered through a pad of hydrous magnesium silicate. The volatiles are removed by distillation to dryness to give a solid (234 g, 92%, 95% HPLC area purity). $^1$H NMR (DMSO-$D_6$): 9.56 (d, 1H, J=0.9 Hz), 8.93 (m, 2H), 7.60 (m, 2H).

EXAMPLE 5

6-chloro-2-pyrazin-2-yl-N-[(1S)-2,2,2-trifluoro-1-methylethyl]-5-(2,4,6-trifluorophenyl)pyrimidin-4-amine To 4,6-dichloro-2-pyrazin-2-yl-5-(2,4,6-trifluoro-phenyl)-pyrimidine (40 g, 0.112 mol) in 1-methyl-2-pyrrolidinone (40 mL) there is added (S)-2,2,2-trifluoro-1-methylethylamine (31.6 g, 0.28 mol). The mixture is sealed and heated to 110° C. and stirred for 24 h. The reaction mixture is cooled to room temperature and diluted with IPA (120 mL) and water (120 mL) added slowly over 30 minutes to form a solid. The solid is filtered and washed with water (2×60 mL) to give 6-chloro-2-pyrazin-2-yl-N-[(1S)-2,2,2-trifluoro-1-methylethyl]-5-(2,4,6-trifluorophenyl)pyrimidin-4-amine in 84% yield and having a 98% HPLC purity and an enantiomeric excess of >99%. $^1$H NMR (DMSO-$D_6$): 9.58 (d, 1H, J=1.1 Hz), 8.85 (m, 2H), 7.72 (d, 1H, J=8.8 Hz), 7.49 (m, 2H), 5.52 (m, 1H), 1.35 (d, 3H, J=7.0 Hz).

EXAMPLE 6

6-Chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine and its hemifumarate salt To a solution of potassium t-butoxide (KOt-Bu) (27.1 g, 0.242 mol) in anhydrous tetrahydrofuran (THF) (175 mL)

there is added 3-methylamino-propan-1-ol (18.5 g,0.208 mol) at room temperature (23±2° C.) dropwise over 30 min. The mixture is stirred for 30 min followed by addition of a solution of 6-chloro-2-pyrazin-2-yl-N-[(1S)-2,2,2-trifluoro-1-methylethyl]-5-(2,4,6-trifluorophenyl)pyrimidin-4-amine (35.0 g, 0.0806 mol) in THF (70 mL) over 15 min. The mixture is stirred for 23 h. The reaction mixture is added to cold water (245 mL) (5–15° C.) while the temperature is maintained between 5–15° C. The reaction mixture is extracted with EtOAc (250 mL). The organic phase is washed with 10% sodium chloride (NaCl) aqueous solution and dried over magnesium sulfate (MgSO$_4$) and filtered giving a filtrate containing 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine.

A solution of fumaric acid (4.67 g, 0.0403 mol) in ethanol (250 mL) is added slowly to the filtrate and the mixture is stirred for 1 h. The solid product is filtered, washed with ethanol (3×70 mL) and dried at 25° C./10 mmHg for 20 h to give a white solid in 80% yield and >99% HPLC area purity and 99% ee.

NMR indicates the ratio of acid to base is 0.5 to 1. $^1$H NMR (DMSO-D$_6$): δ 9.57 (d, 1H, J=1.2 Hz), 8.84 (m, 2H), 7.71 (d, 1H, J=8.8 Hz), 6.96 (m, 2H), 6.40 (s, 1H, proton on fumaric acid double bond), 5.53 (m, 1H), 4.16 (t, 2H, J=6.1), 2.85 (t, 2H, J=7.1), 2.45 (s, 3H), 2.04 (m, 2H), 1.37 (d, J=7.1, 3H).

What is claimed is:

1. 6-Chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate.

2. A process for the preparation of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate; which process comprises: reacting 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine of the formula

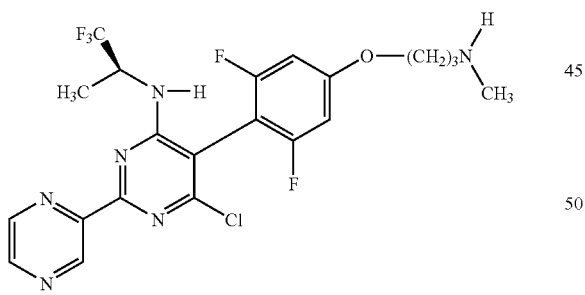

in an aprotic solvent with fumaric acid in an alcohol to give said hemifumarate.

3. A process for the preparation of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate;

which process comprises the steps of:
a. reacting pyrazine-2-carbonitrile with a base selected from the alkali metal alkoxide or alkali metal hydroxide in an alcohol and treating with an ammonium salt of an inorganic acid to give a pyrazine-2-carboxamidine inorganic acid salt;

b. reacting the pyrazine-2-carboxamidine inorganic acid salt with a malonic acid ester of the formula

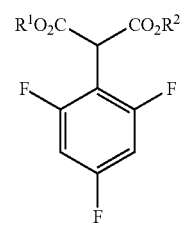

where $R^1$ and $R^2$ are independently $C_{1-C3}$ alkyl in an aprotic solvent in the presence of a base and acidifying to obtain 2-pyrazin-2-yl-5-(2,4,6-trifluorophenyl)-pyrimidine-4,6-diol of the formula

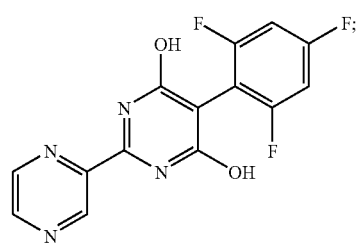

c. chlorinating the 2-pyrazin-2-yl-5-(2,4,6-trifluorophenyl)-pyrimidine-4,6-diol with phosphorus oxychloride (POCl$_3$) as chlorinating reagent in the presence of an amine base in an aprotic solvent to give 4,6-dichloro-2-pyrazin-2-yl-5-(2,4,6-trifluorophenyl)-pyrimidine of the formula

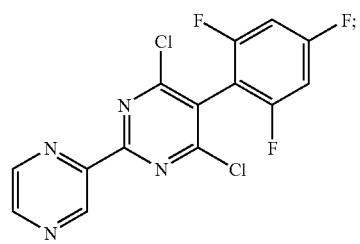

d. reacting the 4,6-dichloro-2-pyrazin-2-yl-5-(2,4,6-trifluoro-phenyl)-pyrimidine with (S)-2,2,2-trifluoro-1-methyl-ethylamine having the formula

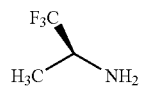

in an aprotic solvent to give 6-chloro-2-pyrazin-2-yl-N-[(1S)-2,2,2-trifluoro-1-methylethyl]-5-(2,4,6-trifluorophenyl)pyrimidin-4-amine having the formula

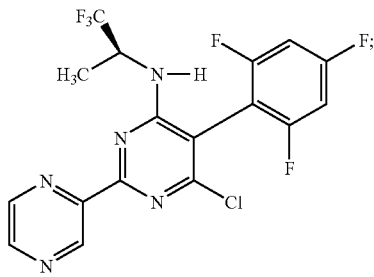

e. reacting 3-methylamino-propan-1-ol with base selected from an alkali metal alkoxide and alkali metal hydride in an aprotic solvent and adding 6-chloro-2-pyrazin-2-yl-N-[(1S)-2,2,2-trifluoro-1-methylethyl]-5-(2,4,6-trifluorophenyl)pyrimidin-4-amine to give 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine of the formula

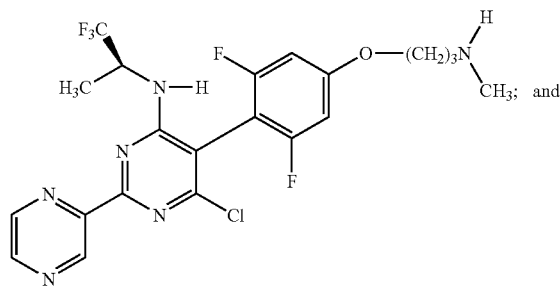

f. reacting the 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine in an aprotic solvent with fumaric acid in an alcohol to give said hemifumarate.

4. A process according to claim 3, wherein in step a the alcohol is methanol.

5. A process according to claim 3, wherein in step a the ammonium salt of an inorganic acid is ammonium chloride.

6. A process according to claim 3, wherein step a further comprises dilution with methyl t-butyl ether and collecting the pyrazine-2-carboxamidine inorganic acid salt.

7. A process according to claim 3, wherein the base in step a is an alkali metal alkoxide.

8. A process according to claim 7 wherein the alkali metal alkoxide is sodium methoxide in a mole ratio of about 1:1 with pyrazine-2-carbonitrile.

9. A process according to claim 8, wherein step a is carried out at a temperature of about 20–40° C. for about 3–12 h.

10. A process according to claim 3 wherein step a is carried out at a temperature of about 25° C. for about 16–48 h and adding methyl t-butyl ether.

11. A process according to claim 3, wherein in step b the ratio of pyrazine-2-carboxamide inorganic acid salt to malonic acid ester of the formula

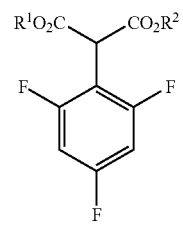

is about 1:1 (mole/mole) to about 1:1.5(mole/mole).

12. A process according to claim 3, wherein in step b the base is selected from an alkali metal hydroxide, alkali metal carbonate and alkali metal hydride or an amine base selected from 1,8-diazabicyclo[4.3.0]non-5-ene(DBU), N,N-diisopropylethylamine, and triethylamine.

13. A process according to claim 11 wherein the ratio of pyrazine-2-carboxamide inorganic acid salt to malonic acid ester of the formula

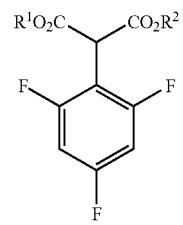

is about 1:1.2 (mole/mole).

14. A process according to claim 12 wherein the base in step b is an alkali metal carbonate.

15. A process according to claim 14 wherein the base in step b is potassium carbonate.

16. A process according to claim 3, wherein in step b the aprotic solvent is selected from N,N-dimethylformamide, 1-methyl-2-pyrrolidinone (NMP) and 2-methoxyethyl ether (diglyme).

17. A process according to claim 3, wherein in step b the aprotic solvent is 2-methoxyethyl ether (diglyme) and the base is potassium carbonate.

18. A process according to claim 3, wherein in step b the aprotic solvent is 1-methyl-2-pyrrolidinone (NMP) and the base is DBU.

19. A process according to claim 3, wherein in step b the ratio of pyrazine-2-carboxamide inorganic acid salt to malonic acid ester of the formula

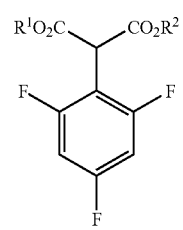

is 1:1.2, wherein the base is DBU in NMP.

20. A process according to claim 3, wherein step b further comprises adjusting the pH to about 1 to 3.

21. A process according to claim 20 wherein the pH in step b is adjusted with acetic acid followed by a mineral acid.

22. A process according to claim 3, wherein in step b the reaction is carried out at a temperature of about 80° C. to about 180° C. in diglyme and the base is potassium carbonate.

23. A process according to claim 3, wherein in step b the reaction temperature is about 95° C. in NMP with the base DBU.

24. A process according to claim 3, wherein in step c the aprotic solvent is toluene.

25. A process according to claim 24 wherein the toluene is about 5–15 mL per gram of the 2-pyrazin-2-yl-5-(2,4,6-trifluoro-phenyl)-pyrimidine-4,6-diol.

26. A process according to claim 3, wherein in step c the molar ratio of phosphorus oxychloride (POCl$_3$) to N,N-diisopropylethyl amine is about 1:1 to about 1:5.

27. A process according to claim 26 wherein the molar ratio of POCl$_3$ to N,N-diisopropylethyl amine is about 1:4.

28. A process according to claim 3, wherein in step c the mixture is heated to reflux for about 6 to 24 h.

29. A process according to claim 3, wherein in step d the aprotic solvent is 1-methyl-2-pyrrolidinone (NMP).

30. A process according to claim 29 wherein the ratio of NMP(ml) per g of 4,6-dichloro-2-pyrazin-2-yl-5-(2,4,6-trifluorophenyl)-pyrimidine is about 1–10 ml per g.

31. A process according to claim 30 wherein the ratio of NMP(ml) per g of 4,6-dichloro-2-pyrazin-2-yl-5-(2,4,6-trifluorophenyl)-pyrimidine is about 1–5 ml/g.

32. A process according to claim 3, wherein in step d the ratio of 4,6-dichloro-2-pyrazin-2-yl-5-(2,4,6-trifluorophenyl)-pyrimidine to (S)-2,2,2-trifluoro-1-methyl-ethylamine is about 1:2–1:3.

33. A process according to claim 32 wherein the ratio of 4,6-dichloro-2-pyrazin-2-yl-5-(2,4,6-trifluorophenyl)-pyrimidine to (S)-2,2,2-trifluoro-1-methyl-ethylamine is about 1:2.5 and the step further comprises heating at about 90° C. to about 125° C. for about 24–48 h.

34. A process according to claim 3, wherein step d is carried out in a sealed system.

35. A process according to claim 3 wherein in step d the mixture is poured into water at about 10–20° C. in a ratio of NMP to water(v/v) of about 1:1–1:5.

36. A process according to claim 35 wherein the ratio of NMP to water is about 1:2(v/v).

37. A process according to claim 3 wherein in step e the base is an alkali metal alkoxide.

38. A process according to claim 37 wherein the alkali metal alkoxide in step e is potassium t-butoxide.

39. A process according to claim 3 wherein in step e the aprotic solvent is anhydrous tetrahydrofuran (THF) or dimethylsulfoxide (DMSO).

40. A process according to claim 3 wherein in step f the aprotic solvent is ethyl acetate and the alcohol is ethyl alcohol.

41. A process for the preparation of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate;

which process comprises the steps of:
a. reacting pyrazine-2-carbonitrile with sodium methoxide in methyl alcohol and treating with ammonium chloride to afford pyrazine-2-carboxamidine hydrochloride;

b. reacting pyrazine-2-carboxamidine hydrochloride with 2-(2,4,6-trifluorophenyl)malonic acid diethyl ester of the formula

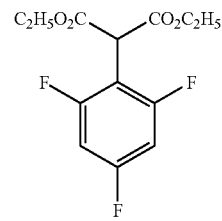

in diglyme in the presence of potassium carbonate and acidifying to obtain 2-pyrazin-2-yl-5-(2,4,6-trifluorophenyl)-pyrimidine-4,6-diol of the formula

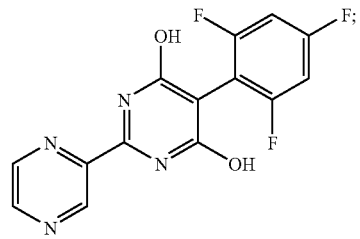

c. halogenating the 2-pyrazin-2-yl-5-(2,4,6-trifluoro-phenyl)-pyrimidine-4,6-diol with phosphorous oxychloride in the presence of N,N-diisopropylethylamine in toluene to obtain 4,6-dichloro-2-pyrazin-2-yl-5-(2,4,6-trifluoro-phenyl)-pyrimidine of the formula

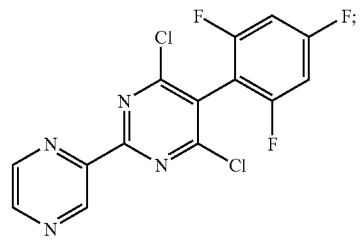

d. reacting the 4,6-dichloro-2-pyrazin-2-yl-5-(2,4,6-trifluoro-phenyl)-pyrimidine compound with (S)-2,2,2-trifluoro-1-methyl-ethylamine having the formula

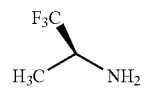

in 1-methyl-2-pyrrolidinone to obtain 6-chloro-2-pyrazin-2-yl-N-[(1S)-2,2,2-trifluoro-1-methylethyl]-5-(2,4,6-trifluorophenyl)pyrimidin-4-amine of the formula

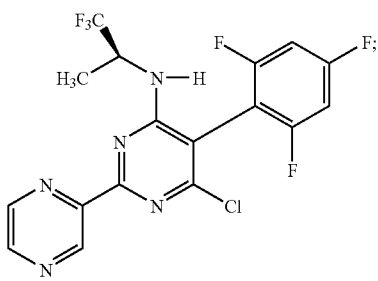

e. reacting an aminoalcohol HO—(CH₂)₃—NHCH₃ with potassium t-butoxide in tetrahydrofuran and adding the 6-chloro-2-pyrazin-2-yl-N-[(1S)-2,2,2-trifluoro-1-methylethyl]-5-(2,4,6-trifluorophenyl)pyrimidin-4-amine to obtain 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine of the formula

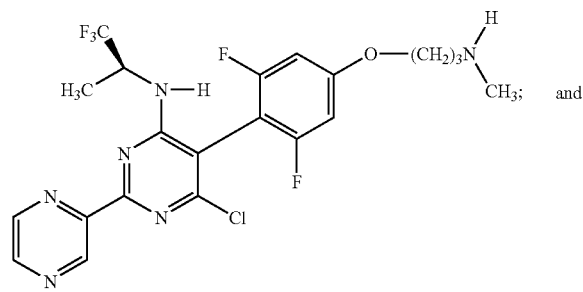

f. reacting the 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine in ethyl acetate with fumaric acid in ethyl alcohol to obtain said hemifumarate.

42. The process according to claim 41, wherein in step f the ratio of ethyl acetate to ethyl alcohol is 1:1 (v/v).

43. A process for the preparation of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate which process comprises the steps of:

a. reacting an aminoalcohol HO—(CH₂)₃—NHCH₃ with potassium t-butoxide in tetrahydrofuran and adding 6-chloro-2-pyrazin-2-yl-N-[(1S)-2,2,2-trifluoro-1-methylethyl]-5-(2,4,6-trifluorophenyl)pyrimidin-4-amine of the formula

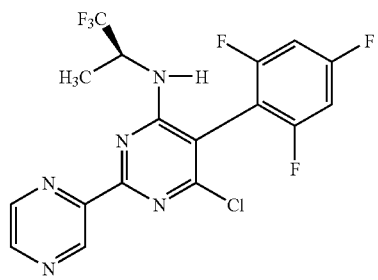

at ambient temperature to give 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine of the formula

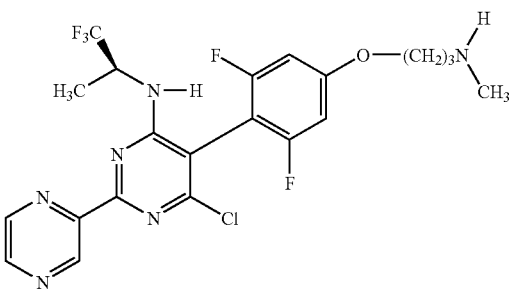

b. adding a solution of fumaric acid in ethyl alcohol to a solution of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine in ethyl acetate to give said hemifumarate; and c. isolating said hemifumarate.

44. The compound 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate produced by the process which comprises:

a. reacting an aminoalcohol HO—(CH₂)₃—NHCH₃ with potassium t-butoxide in tetrahydrofuran and adding 6-chloro-2-pyrazin-2-yl-N-[(1S)-2,2,2-trifluoro-1-methylethyl]-5-(2,4,6-trifluorophenyl)pyrimidin-4-amine of the formula

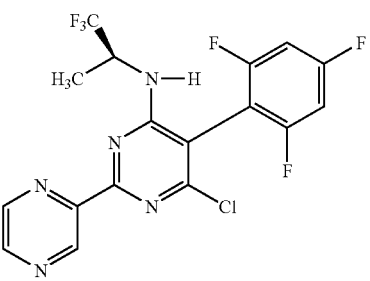

at ambient temperature to give 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine of the formula

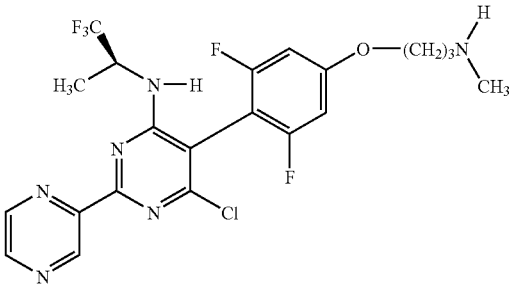

b. adding a solution of fumaric acid in ethyl alcohol to a solution of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine in ethyl acetate to give said hemifumarate; and c. isolating said hemifumarate.

45. A pharmaceutical composition which comprises an effective amount of 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hemifumarate with a pharmaceutically acceptable carrier.

46. The process according to claim 2 wherein the aprotic solvent is ethyl acetate and the alcohol is ethyl alcohol.

47. The process according to claim 46 wherein the ratio of ethyl acetate:ethyl alcohol is 1:1 (v/v).

* * * * *

UNITED STATES PATENT AND TRADEMARK OFFICE
CERTIFICATE OF CORRECTION

| | | |
|---|---|---|
| PATENT NO. | : 7,244,736 B2 | Page 1 of 1 |
| APPLICATION NO. | : 11/451078 | |
| DATED | : July 17, 2007 | |
| INVENTOR(S) | : David Michael Blum et al. | |

It is certified that error appears in the above-identified patent and that said Letters Patent is hereby corrected as shown below:

On the Title Page

Item (75) the following Inventors should be added – Sherry Mannching Ku, Thiells, NY and Fang Fang Qu, New City, NY Signed and Sealed this Twenty-fourth Day of August, 2010

David J. Kappos
*Director of the United States Patent and Trademark Office*